(12) United States Patent
Abousaleh

(10) Patent No.: US 10,345,174 B2
(45) Date of Patent: Jul. 9, 2019

(54) DEVICE FOR MEASURING A PRESSURE IN A FLUID AND PUMP PROVIDED WITH SUCH A DEVICE

(71) Applicant: Khaled Abousaleh, Schindellegi (CH)

(72) Inventor: Khaled Abousaleh, Schindellegi (CH)

(*) Notice: Subject to any disclaimer, the term of this patent is extended or adjusted under 35 U.S.C. 154(b) by 0 days.

(21) Appl. No.: 15/590,069

(22) Filed: May 9, 2017

(65) Prior Publication Data
US 2017/0328796 A1 Nov. 16, 2017

(30) Foreign Application Priority Data
May 10, 2016 (FR) ...................................... 16 54151

(51) Int. Cl.
*G01L 1/22* (2006.01)
*G01L 7/02* (2006.01)
*G01L 9/00* (2006.01)
*G01L 11/02* (2006.01)

(52) U.S. Cl.
CPC ................ *G01L 7/022* (2013.01); *G01L 1/22* (2013.01); *G01L 9/00* (2013.01); *G01L 9/0044* (2013.01); *G01L 9/0051* (2013.01); *G01L 11/02* (2013.01); *A61B 2562/0247* (2013.01); *A61B 2562/0261* (2013.01)

(58) Field of Classification Search
CPC .................................. G01L 7/022; G01L 11/02
USPC ........................................................... 73/730
See application file for complete search history.

(56) References Cited

U.S. PATENT DOCUMENTS

| | | | |
|---|---|---|---|
| 2006/0211914 A1* | 9/2006 | Hassler, Jr. | ........... A61F 5/0003 600/37 |
| 2011/0144531 A1* | 6/2011 | Marcotte | ............... A61B 5/1116 600/561 |
| 2013/0145866 A1* | 6/2013 | Abousaleh | .............. F04B 49/00 73/863.01 |

OTHER PUBLICATIONS

FR Search Report, dated Jan. 13, 2017, from corresponding FR application.

* cited by examiner

*Primary Examiner* — Jamel E Williams
(74) *Attorney, Agent, or Firm* — Young & Thompson

(57) ABSTRACT

Disclosed is a sensor to measure a pressure in a fluid, of which a body 1 includes a membrane 2 and a wall 3 forming a peripheral support for and around the membrane. The membrane and the peripheral wall are formed from one single component, and the membrane and the peripheral wall together form a flat and smooth front surface 4 intended to be in contact with the fluid.

20 Claims, 1 Drawing Sheet

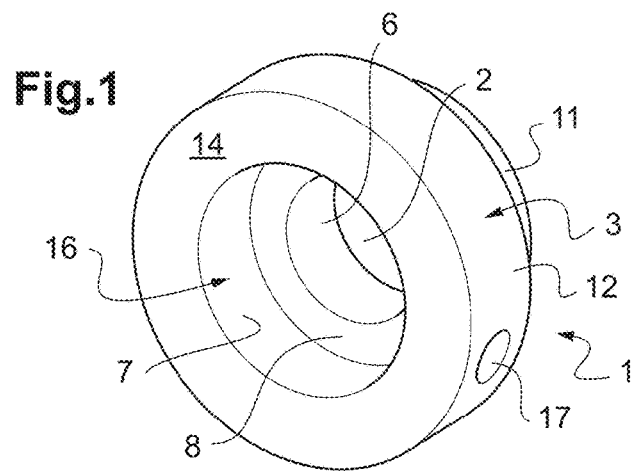
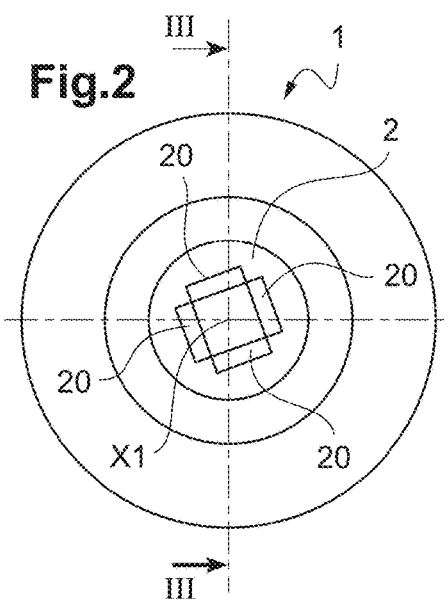
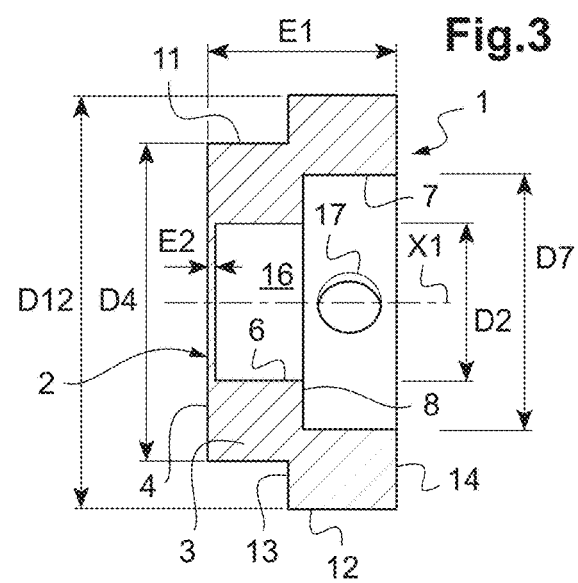
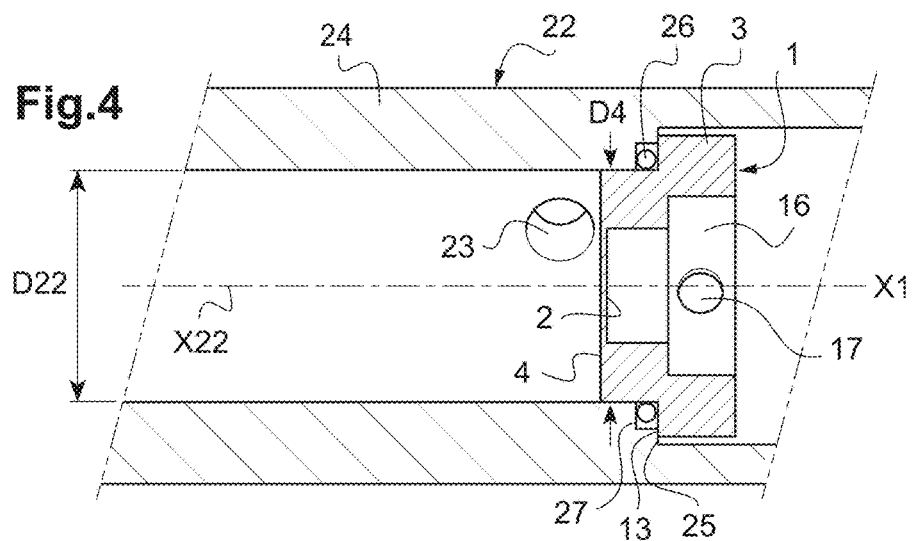

DEVICE FOR MEASURING A PRESSURE IN A FLUID AND PUMP PROVIDED WITH SUCH A DEVICE

FIELD OF THE INVENTION

This invention relates to the field of pressure sensors, in particular membrane sensors, in particular small-sized membrane sensors.

BACKGROUND OF THE INVENTION

It is known that such sensors comprising a membrane are realised by welding or bonding on a general ring-shaped case. When such a sensor is used to measure the pressure in a liquid, gas bubbles come to be fixed on the junction between the case and the membrane. This can be all the more detrimental to the quality of the measurements as the sensor is small and as the pressure levels to be measured are low.

In addition, when the membrane is welded or bonded according to the prior art, there is a phenomenon which appears when the membrane is deformed and which is called an "oil can effect". Indeed, the deformation of the membrane is non-linear when we pass from a positive pressure to a negative pressure, or vice versa.

In addition, the different materials used to produce the sensor, in particular welds or adhesives, are not always chemically and/or biologically compatible with the fluid of which the pressure is to be measured. Thus, in particular, corrosion can appear at the junction between the membrane and the case, which is detrimental to the lifespan of the sensor and/or to the preservation of the fluid.

SUMMARY OF THE INVENTION

The invention aims to offer means to produce a sensor which can be small in size, while guaranteeing an improved lifespan and great quality in taking measurements.

To achieve its aim, the invention offers a body for a sensor, intended to measure a pressure in a fluid, in particular in a liquid, comprising a membrane and a wall forming a peripheral support for and around this membrane, characterised in that:

the membrane and the peripheral wall are formed from one single component; and, the membrane and the peripheral wall together form a front surface, substantially flat and smooth, intended to be in contact with the fluid.

Preferably, the peripheral wall is ring-shaped and defines, behind the membrane, a compartment, in particular for at least one strain gauge.

The invention also offers a sensor for measuring a pressure in a fluid, characterised in that it comprises a body according to the invention and at least one strain gauge, positioned on a rear face of the membrane, opposite the front face.

The invention also offers a device for pumping a fluid, in particular a precision pump, characterised in that it comprises a cylindrical pumping chamber around an axis, this chamber being axially closed by the front surface of a body according to the invention.

The invention also offers a device for measuring a pressure in a living organism, in particular human, characterised in that it comprises a sensor according to the invention, the sensor being provided to be implanted in this organism, this device additionally comprising wireless reading means of a measurement, preferably of radiofrequency type, in particular known as the acronym RFID.

BRIEF DESCRIPTION OF THE DRAWINGS

Several implementation methods of the invention will be described below, as non-exhaustive examples, referenced to appended drawings, wherein:

FIG. 1 is a perspective view of the body of a sensor according to the invention;

FIG. 2 is an axial view of the inside of the body of FIG. 1;

FIG. 3 is a longitudinal cross-sectional view of the body according to plan of FIG. 2; and, FIG. 4 is a longitudinal view of the body, in a usage position at the end of a pumping chamber.

DETAILED DESCRIPTION OF THE INVENTION

The figures illustrate a body 1 of a pressure sensor. The body 1 substantially has a circular shape around an axis X1; it is formed from one single component. It comprises:

a front wall 2, acting as a membrane 2 for the sensor; and,
a ring-shaped wall 3.

The front wall, of low thickness E2, is in a circular axis disc shape X1 and the membrane has a diameter D2. The ring-shaped wall constitutes a peripheral wall acting as a support for the membrane 2. The membrane 2 and the ring-shaped wall 3 together form a substantially flat and smooth front surface 4. This front surface 4 extends radially from the axis X1, in the shape of a disc, which has a front diameter D4.

The ring-shaped wall 3 defines:

a first cylindrical interior surface 6, of diameter D2;
a second cylindrical interior surface 7, of diameter D7>D2;
a ring-shaped interior surface 8, extending radially between the two interior surfaces 6 and 7, and forming with them, an interior shoulder;
a first cylindrical exterior surface 11, of diameter D4;
a second cylindrical exterior surface 12, of diameter D12 forming the largest diameter of the body, with D12>D4;
a ring-shaped exterior surface 13, extending radially between the two exterior surfaces 11 and 12, and forming with them, an exterior shoulder; and,
a ring-shaped rear surface 14, extending radially between the second interior surface 7 and the second exterior surface 12.

The interior surfaces together define a compartment 16. In the example illustrated, the ring-shaped wall 3 is pierced with a hole 17 extending radially; this hole leads, on the one hand, through the first interior surface 7 and on the other hand, through the second exterior surface 12.

The compartment 16 is, in particular, provided to contain the strain gauges 20, visible in FIG. 1. The hole 17 enables the passing of wires connecting the gauges 20 with means, not represented, to handle the deformations of the membrane detected by the gauges. In the example illustrated, the sensor comprises four gauges 20 fixed behind the membrane 2 perpendicularly to each other.

As illustrated in FIG. 4, a sensor according to the invention can be used to measure a pressure in a pumping chamber 22.

In the example illustrated, the pumping chamber is cylindrical around an axis X22. The diameter D22 of the chamber is substantially equal to the front diameter D4 of the body 1.

The body 1 is entered at an axial end of the chamber 22, so that the axis X1 of the body and the axis X22 of the chamber are substantially taken together, the front surface 4 thus constituting a base for the chamber 22, opposite to a piston, not represented. An orifice is formed laterally in a wall 24 of the chamber, for the admission and/or expulsion of the fluid to be pumped. This orifice is positioned so that it is flush with the front surface 4, i.e. the base 4 of the chamber. The ring-shaped exterior surface 13 of the body 1 is provided to axially abut against a first shoulder 25 of the wall 24 of the chamber 22; an axial positioning of the front wall 4 in the chamber is thus ensured. Additionally, a watertight toric seal 26 is assembled compressed between the ring-shaped exterior wall 13 and a second shoulder 27 of the wall 24.

The interest in achieving watertightness against the ring-shaped exterior surface 13 is to decrease the impact of tightening constraints on the membrane and the strain gauges. It is a major impact of the shape of this sensor. Most sensors on the market achieve watertightness on the front surface 4 next to the membrane which aims to deform this, and therefore to interfere with the measurement. The other benefit of not achieving watertightness on the front surface 4 is that this surface remains flat and enables the circulation of liquids tangentially to the membrane without trapping gas or particles.

The membrane 2 has a significant tensile $D2/E2$. Its thickness $E2$ is low in relation to the thickness $E3=(D4-D2)/2$ of the ring-shaped wall 3 at the front surface 4, so that the ring-shaped wall is rigid in relation to the membrane. In the example illustrated, the dimensions of the sensor are substantially:

$E1=3.6$ mm
$E2=0.06$ mm
$E3=1.25$ mm
$D2=3.5$ mm
$D4=6$ mm
$D12=8$ mm

Preferably, for a sensor according to the invention, the following are chosen:

0.01 mm<$E2$<1 mm
and
1 mm<$D2$<5 mm

Preferably, the body of the sensor is made of stainless steel or titanium or a stainless-steel derivative; it can be made by machining or 3D printing.

Of course, the invention is not limited to the preferred embodiments that have just been described, but, conversely, the invention is defined by the following claims.

Indeed, it appears to a person skilled in the art, that various modifications can be brought about to the embodiments described above, in light of the information which has just been disclosed to them.

Thus, instead of four gauges, the sensor can comprise a different number of these; they can be positioned differently.

One sensor according to the invention is adapted to fit a precision pump. It can also fit another device.

One sensor according to the invention is particularly beneficial, indeed:

it is a sensor of which the membrane is deformed, and of which the strain gauges, positioned inside, enable to measure the movement variations of the membrane;

the body is made from one single component without being welded or bonded; the material that constitutes it has, because of this, an optimised performance as the deformations of the membrane happen in the elastic area of the material, and the lifespan of the sensor is increased;

the absence of weld and adhesive enable its miniaturisation;

the absence of weld and adhesive, eliminating any porosity risk, enables optimal chemical and biological compatibility;

the flush membrane, in other words, forming one single and same front surface with the ring-shaped wall, is optimised for liquids, as it does not hold gas bubbles; the precision in measuring the pressure is improved and the performance of the device provided with such a sensor is optimised;

the full pressure range and the over pressure are increased, using the elastic resistance of the material, of which the body of the sensor is fully constituted;

it is not sensitive to vibrations nor noises, only variations in pressure, the relationship between the thickness of the ring-shaped wall of the body and that of the membrane being highly increased;

by its dimensional characteristics and biological compatibility, this sensor can be wirelessly implanted in the human body as it is reliable and has a long lifespan;

in addition, the gauges used consume a low current, which enables to obtain an implantable product; this sensor can even be passive (with no battery), as the gauges require low activation energy;

this sensor uses miniature semiconductor gauges which have a gauge factor equal to 200, a lot higher than the gauge factor of metal gauges, which is 3; which enables very low deformations to be measured;

with a machined membrane according to the invention, the "oil can" effect is corrected, as the linearity of the deformation is kept; this correction enables the lowest pressures to be measured and low variations in negative/positive pressure to be measured, by having a deformation which remains linear.

Another interest of a sensor according to the invention is that the strain gauges can be directly applied on the membrane (electrically insulated), so that when there is a deformation of the membrane, there is a direct transmission of this deformation on the gauges; this enables to obtain a precise measurement, and enables low deformations to be measured. Conversely, sensors on the market often contain a viscous liquid or oil, in order to transmit the deformation of the membrane to the sensitive element, which leads to a loss of sensitivity and precision in the measurement. In addition, gas bubbles are likely to be present in the liquids used, which leads to a shock absorption in the transmission of the pressure and a sensitivity to room temperature and general pressure.

The invention claimed is:

1. A sensor for measuring a pressure in a fluid, the sensor comprising:

a body (1) comprised of a sensor membrane (2) and a peripheral wall (3) forming a peripheral support for and around said sensor membrane, wherein, said sensor membrane and said peripheral wall are formed from one single component, the body being a single component free of welded and bonded parts, and said membrane and said peripheral wall together form a front surface (4) substantially flat and smooth, intended to be in contact with said fluid; and at least one strain gauge (20) positioned on a rear face of the sensor membrane (2) opposite the front surface (4) to measure the movement variations of the sensor membrane, and wherein plural of the at least one strain gauge (20) are positioned on a rear face of the sensor membrane (2) opposite the front surface (4).

2. The sensor according to claim 1, wherein the peripheral wall (3) of the body (1) is ring-shaped and defines, behind the sensor membrane (2), a compartment (16) housing said at least one strain gauge (20).

3. The sensor according to claim 2, wherein the sensor membrane (2) has a thickness (E2) of between 0.01 mm and 1 mm inclusive, and a diameter (D2) of between 1 mm and 5 mm inclusive.

4. The sensor according to claim 1, wherein the body is made of steel and is a single component comprising machined surfaces free of welded parts and bonded parts.

5. The sensor according to claim 4, wherein the sensor membrane (2) has a thickness (E2) of between 0.01 mm and 1 mm inclusive, and a diameter (D2) of between 1 mm and 5 mm inclusive.

6. The sensor according to claim 1, wherein the body is made of steel and is a single 3D printed component free of welded parts and bonded parts.

7. The sensor according to claim 6, wherein the sensor membrane (2) has a thickness (E2) of between 0.01 mm and 1 mm inclusive, and a diameter (D2) of between 1 mm and 5 mm inclusive.

8. The sensor according to claim 1, wherein the sensor membrane (2) has a thickness (E2) of between 0.01 mm and 1 mm inclusive, and a diameter (D2) of between 1 mm and 5 mm inclusive.

9. The sensor according to claim 8, wherein the body is made of titanium and is a single component comprising machined surfaces free of welded parts and bonded parts.

10. The sensor according to claim 8, wherein the body is made of titanium and is a single 3 D printed component free of welded parts and bonded parts.

11. The sensor according to claim 8, wherein the body is a single titanium component.

12. The sensor according to claim 8, wherein the body is a single steel component.

13. The sensor according to claim 1, further comprising a cylindrical pumping chamber (22) around an axis (X22), said pumping chamber being axially closed by the front surface (4) of a body (1), the at least one strain gauge (20) positioned on a rear face of the sensor membrane (2) opposite the front surface (4) to measure the movement variations of the sensor membrane to measure a pressure in the cylindrical pumping chamber (22).

14. The sensor according to claim 1, further comprising wireless reading means of a measurement of the at least one strain gauge (20), said sensor configured for implantation in a human body.

15. The sensor of claim 14, wherein the wireless reading means of a measurement is a RFID device.

16. A sensor for measuring a pressure in a fluid, the sensor comprising:
a body (1) comprised of a sensor membrane (2) and a wall (3) forming a peripheral support for and around said sensor membrane, wherein,
said sensor membrane and said peripheral wall are formed from one single component, and
said membrane and said peripheral wall together form a front surface (4) substantially flat and smooth, intended to be in contact with said fluid; and
plural strain gauges (20) positioned on a rear face of the sensor membrane (2) opposite the front surface (4), the plural strain gauges (20) positioned to measure the movement variations of the sensor membrane,
wherein the sensor membrane (2) has a thickness (E2) of between 0.01 mm and 1 mm inclusive, and a diameter (D2) of between 1 mm and 5 mm inclusive, and
wherein the body is a single steel or titanium component free of welded and bonded parts.

17. A sensor for measuring a pressure in a fluid, the sensor comprising:
a body (1) comprised of a sensor membrane (2) and a wall (3) forming a peripheral support for and around said sensor membrane, wherein,
said sensor membrane and said peripheral wall are formed from one single component, and
said membrane and said peripheral wall together form a front surface (4) substantially flat and smooth, intended to be in contact with said fluid; and
four strain gauges (20) fixed behind the sensor membrane perpendicularly to each other, the strain gauges (20) positioned to measure the movement variations of the sensor membrane,
wherein the sensor membrane (2) has a thickness (E2) of between 0.01 mm and 1 mm inclusive, and a diameter (D2) of between 1 mm and 5 mm inclusive, and
wherein the body is a single steel or titanium component free of welded and bonded parts.

18. The sensor according to claim 16, further comprising a cylindrical pumping chamber (22) around an axis (X22), said pumping chamber being axially closed by the front surface (4) of a body (1), the plural of the at least one strain gauge (20) positioned on a rear face of the sensor membrane (2) opposite the front surface (4) to measure the movement variations of the sensor membrane to measure a pressure in the cylindrical pumping chamber (22).

19. The sensor according to claim 18, further comprising wireless reading means of a measurement of the at least one strain gauge (20), said sensor configured for implantation in a human body.

20. The sensor of claim 19, wherein the wireless reading means of a measurement is a RFID device.

* * * * *